(12) United States Patent
Maatta et al.

(10) Patent No.: US 6,706,833 B1
(45) Date of Patent: Mar. 16, 2004

(54) POLYMERS INCORPORATING COVALENTLY ATTACHED ORGANOIMIDO POLYOXOMETALATES

(75) Inventors: Eric A. Maatta, Manhattan, KS (US); Aaron R. Moore, Summerville, SC (US)

(73) Assignee: Kansas State University Research Foundation, Manhattan, KS (US)

( * ) Notice: Subject to any disclaimer, the term of this patent is extended or adjusted under 35 U.S.C. 154(b) by 258 days.

(21) Appl. No.: 09/609,863

(22) Filed: Jul. 6, 2000

(51) Int. Cl.$^7$ ................................................ G08F 30/04
(52) U.S. Cl. ................... 526/240; 526/346; 526/329.7; 526/274; 526/236
(58) Field of Search ............................. 526/346, 329.7, 526/274, 236, 240

(56) References Cited

U.S. PATENT DOCUMENTS 5,391,638 A  2/1995  Katsoulis et al.

FOREIGN PATENT DOCUMENTS

WO  723970 A2  7/1996

OTHER PUBLICATIONS

Moore, Hexamolybdate Complexes bearing Organoimido Ligands with Remote Functionality, Kansas State U., 1998.*
Mayer, Cedric R. et al., Incorporation of Magnetic Nanoparticles in New Hybrid Networks Based on Heteropolyanious and Polyacrylamide; *Agnew. Chem. Int. Ed.* 1999, 38, No. 24; pp. 3672–3675.

Katsoulis, D.E., *Chem. Rev.*, A Survey of Applications of Polyoxometalates, 1998, 359–387.

Knoth, W.H., *J. Am. Chem. Soc.*, Derivatives of Heteropolyanions, 1979, 2211–2213.

Katsoulis, D.E. et al., *Mater. Res. Soc. Symp. Proc.*, Silicon–Polyoxometalate (SiPOM) Hybrid Compounds, 1996, 589–594.

Judeinstein, P. *Chem. Mater.*, Synthesis and Properties of Polyoxometalates Based Inorganic–Organic Polymers, 1992, 4–7.

Moore, A.R., Hexamolybdate Complexes Bearing Organoimido Ligands With Remote Functionality, 1998.

* cited by examiner

*Primary Examiner*—Ling-Siu Choi
(74) *Attorney, Agent, or Firm*—Hovey Williams LLP

(57) ABSTRACT

New polyoxometalate compounds and polymers comprising recurring monomers of those compounds are provided. The compounds are formed by replacing at least one oxide of the starting polyoxometalate with an organoimido (NR) group bonded to the polyoxometalate via a triple bond to the nitrogen atom. The R of the (NR) group comprises a reactive functional group which renders the compound readily polymerizable, alone or with other monomers (e.g., divinylbenzene), to form the inventive polymers. Additionally, a countercation (e.g., bis(tetra-n-butylammonium)) can be mixed with the polyoxometalate compounds in order to neutralize the negative charge thereof as well as to make those compounds more soluble in organic solvents.

16 Claims, No Drawings

POLYMERS INCORPORATING COVALENTLY ATTACHED ORGANOIMIDO POLYOXOMETALATES

FEDERALLY SPONSORED RESEARCH/ DEVELOPMENT PROGRAM

This invention was made with government support under Grant De-Fg02-92ER14246 awarded by the United States Department of Energy. The government has certain rights in the invention.

BACKGROUND OF THE INVENTION

1. Field of the Invention

The present invention is broadly concerned with new polyoxometalate compounds and polymers comprising recurring monomers of those compounds. More particularly, the inventive compounds comprise an organoimido group bonded to the polyoxometalate in place of at least one oxide of each starting polyoxometalate compound so as to improve certain properties (e.g., solubility in organic solvents) of the compounds.

2. Description of the Prior Art

Polyoxometalates are soluble, inorganic cluster-like compounds formed principally of an oxide anion and early transition metal cations. These discrete polymeric structures form spontaneously when simple oxides of, for example, vanadium, niobium, tantalum, molybdenum, or tungsten are combined under appropriate conditions in water. In a great majority of polyoxometalates, the transition metals are in the $d^0$ electronic configuration which dictates both high resistance to oxidative degradation and an ability to oxidize other materials. The principal transition metal ions that form polyoxometalates are tungsten(VI), molybdenum(VI), vanadium(V), niobium(V), and tantalum(V).

Isopolyoxometalates, the simplest of the polyoxometalates, are binary oxides of the formula $[M_mO_y]^{p-}$, where m may vary over a wide range of numbers. For example, if m=8 and M=Mo, then the formula is $[Mo_8O_{26}]^{4-}$.

Heteropolyoxometalates have the general formula $[X_xM_mO_y]^{p-}$ and possess a heteroatom, X, at the center thereof. For example, in the α-Keggin structure, $\alpha\text{-}[PW_{12}O_{40}]^{3-}$, X is a phosphorus atom. The central phosphorus atom is surrounded by twelve $WO_6$ octahedra.

Polyoxometalates are characterized by a number of useful structural, electrochemical, catalytic, magnetic, medicinal, and photophysical properties (see, e.g., *Chemical Reviews*, 98:1–389 (1998), incorporated by reference herein). Examples of applications of polyoxometalate systems include: solid state electrochromic devices; electrochemical fuel cells, precursors of oxide films for optoelectronics, recording materials, electrophotography, corrosion-resistant coatings, capacitors, and flammability control/smoke suppression. In the vast majority of these applications, the polyoxometalate species is utilized as an additive, a co-precipitant, or an ionic dopant. That is, the polyoxometalate species is present as a heterogenous additive rather than as a covalently-bonded integral component within the device. There are several disadvantages to using the polyoxometalate species as a heterogenous additive, including a non-uniform distribution of the polyoxometalate species, difficulties in varying the amount of polyoxometalate incorporation, migration and/or loss of polyoxometalate, and poor processability.

There are very few previous examples of polymers bearing covalently-incorporated polyoxometalate species. Knoth, *J. Am. Chem. Soc.*, 101:2211 (1979), incorporated by reference herein, has described an all-inorganic polymer $[(OC)_3CoGe_2W_{11}SiO_{40}^{5-}]_n$. Katsoulis et al., *Mater. Res. Soc. Symp. Proc.*, 435:589 (1996), incorporated by reference herein, have described siloxane polymers bearing polyoxometalate species. Finally, Judeinstein, *Chem. Mat.*, 4:4–7 (1992), incorporated by reference herein, has described the homo-polymerization of systems such as $[Bu_4N]_4[SiW_{11}O_{39}(RSiOSiR)]$, wherein R is vinyl, styryl, allyl, or methacryl group.

SUMMARY OF THE INVENTION

The present invention is broadly concerned with new polyoxometalate compounds as well as polymers comprising recurring monomers of these compounds. These compounds are formed by covalently bonding an organoimido group (NR, where R comprises a polymerizable moiety) to a metal site of the polyoxometalate compound in place of an oxide group.

In one embodiment polyoxometalate compounds according to the invention are represented by the formula:

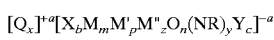

wherein:
each of M, M', and M" is a metal individually selected from the group consisting of Mo, W, V, Ti, Cr, Mn, Fe, Co, Ni, Cu, Zn, Nb, Ru, Rh, Ta, Re, and Os;

R may be the same or different in each (NR) moiety and each R is individually selected from the group consisting of substituted and unsubstituted alkyl and aryl groups other than styrene groups;

each X is individually selected from the group consisting of Si, P, B, As, Se, S, Sn, Sb, and Bi;

each Q may be the same or different, with each Q individually being a cation;

each Y is individually selected from the group consisting of $H_2O$ and the halides;

b is a number ranging from about 0–10, and preferably from about 1–3;

m is a number ranging from about 1–40, and preferably from about 4–18;

each of p and z is individually a number ranging from 0–6, and preferably from about 1–3, with the sum of m, p, and z ranging from 1–40;

n is a number ranging from about 1–200, preferably from about 3–62, and more preferably from about 6–39;

each a is the same number and ranges from about 1–20, and preferably from about 2–12;

each x is a number ranging from about 1–20, and preferably from about 2–12;

c is a number ranging from 0–2, and preferably from about 1–2; and y is a number ranging from about 1–20, and preferably from about 2–6.

As used in the above formula, when b, p, z, and/or c is 0, it is intended that the substituent which b, p, z, or c is quantifying is not present in the compound. For example, if b is 0, then X is not present in the particular polyoxometalate compound.

In one embodiment, both p and z are 0, and M is Mo. In another embodiment, at least one of M and M' is selected from the group consisting of Mo, W, and V, and M" is selected from the group consisting of Ti, Cr, Mn, Fe, Co, Ni, Cu, Zn, Nb, Ru, Rh, Ta, Re, and Os.

In embodiments where a countercation (Q) is present, each countercation is preferably not bonded to the $(X_bM_mM'_pM''_zO_n(NR)_yY_c)$ complex, but is instead physically present therewith in order to counteract the negative charge of the complex. The presence of the countercations can be exploited in several ways such as to increase the solubility of the compounds in organic solvents or to provide for desirable properties through interaction with polyoxometalate components. Each Q is preferably individually selected from the group consisting of $H^+$, alkali metal cations, alkaline earth metal cations, substituted and unsubstituted ammonium cations, substituted and unsubstituted phosphonium cations, and metal complex cations, with bis(tetra-n-butylammonium), lithium cations, and mixtures thereof being the most preferred countercations.

In each of the foregoing embodiments, the nitrogen atom of the (NR) moiety is bonded to a metal atom of the $(X_bM_mM'_pM''_zO_nY_c)$ fragment, preferably via a triple bond. Furthermore, R is preferably a $C_1$–$C_8$ alkyl group or a $C_6$–$C_{12}$ aryl group. Even more preferably, at least one R includes a reactive portion or moiety selected from the group consisting of substituted and unsubstituted vinyl groups (e.g., such as part of an acrylate derivative), substituted and unsubstituted allyl groups, and silyl groups.

When R comprises a vinyl group, that group is represented by the formula —CR'=CH$_2$, wherein R' is selected from the group consisting of hydrogen, substituted and unsubstituted alkyls (preferably $C_1$–$C_6$), substituted and unsubstituted aryls (preferably $C_6$–$C_{10}$), substituted and unsubstituted silanes, substituted and unsubstituted siloxides, and substituted and unsubstituted siloxanes. When R comprises an allyl group, that group is represented by the formula —CR"$_2$—CR"=CH$_2$, wherein each R" is individually selected from the group consisting of hydrogen, substituted and unsubstituted alkyls (preferably $C_1$–$C_6$), substituted and unsubstituted aryls (preferably $C_6$–$C_{10}$), substituted and unsubstituted silanes, substituted and unsubstituted siloxides, and substituted and unsubstituted siloxanes. Finally, when R comprises a silyl group, that group is preferably represented by the formula —SiX'$_p$, wherein each X' is individually selected from the group consisting of the halides, alkoxides, alkyls (preferably $C_1$–$C_8$), aryls (preferably $C_6$–$C_{12}$), alkenyls (preferably $C_1$–$C_8$), and hydrogen, and p is a number ranging from about 1–3.

It will be appreciated that the inventive polyoxometalate compounds can be polymerized (either alone or with other compounds) by conventional polymerization reactions to form new polymers via the R groups on the respective compounds. For example, the desired polyoxometalate compounds according to the invention can be combined in a suitable solvent system with the chosen co-monomer(s) in the desired molar ratio, with a polymerization initiator (if necessary; e.g., 2,2'-azobisisobutyronitrile) being added to the system. Preferably, the compounds are co-polymerized with olefinic monomers and mixtures thereof, and preferably monomers selected from the group consisting of substituted and unsubstituted styrene monomers (e.g., 4-methylstyrene), olefinic monomers (e.g., cross-linking olefins such as divinylbenzenes and silicon-containing olefins such as olefinic silanes, olefinic siloxides, and olefinic siloxanes and their substituted derivatives), acrylates (e.g., methyl methacrylate), vinylic monomers (e.g., vinyl chloride, acrylonitrile, and vinyl acetate), and vinylidene monomers (e.g., vinylidene chloride).

Generally, the solvent systems employed will be non-aqueous systems such as organic solvent systems (e.g., 1,2-dichloroethane and other chlorinated hydrocarbons, toluene, acetonitrile, benzene, and chlorinated aromatic compounds). The polymerization reaction can be carried out over a wide range of temperatures (such as from about 0° C. to about the boiling point of the chosen solvent) depending upon the chosen co-monomers and solvent system. The reaction is preferably carried out at ambient pressures in an oxygen-free atmosphere. Once the complex has been polymerized, the original tetrabutylammonium countercations (if used) are no longer required in order to confer solubility, and may be replaced by other desirable cationic entities.

The polymers according to the invention differ from prior art polyoxometalate polymers in that the polyoxometalate complex is linked to the polymer chain by way of a nitrogen atom rather than an oxygen atom. Furthermore, the overall nature of the polyoxometalate moiety itself is different in that at least one of the oxide groups of the corresponding polyoxometalate compound has been replaced by an isoelectronic organoimido group. This modifies the properties of the polyoxometalate in the following ways: the electronic spectral absorptions of the compounds are shifted in energy and are more intense; the polyoxometalates have enhanced solubility in organic solvent systems; and the electrochemical behavior of the polyoxometalates is modified. Advantageously, these modifications can be controlled by varying the nature and identity of the R of the (NR) moiety as well as by varying the number of (NR) moieties incorporated into the polyoxometalate.

The inventive polyoxometalate compounds and polymers are useful in a wide range of applications. For example, because the polyoxometalates comprising Mo can be incorporated into polymers in a uniform and controlled manner, the polymers are useful as flame retardants and smoke suppressant agents. These polymers would also be useful as precursors for forming $MoO_3$ films. Furthermore, in embodiments where lithium cations are utilized as the countercation, the compounds and polymers can be used to form new classes of materials for ion-conducting applications such as processable ion-conducting materials or polymer electrolytes. Finally, because the polyoxometalate monomers are relatively large and rigid, their use in forming polymers should restrict chain motions within the polymers thus enabling the polymers to be used to form materials which have high temperature uses.

DETAILED DESCRIPTION OF THE PREFERRED EMBODIMENTS

EXAMPLES

The following examples set forth preferred methods in accordance with the invention. It is to be understood, however, that these examples are provided by way of illustration and nothing therein should be taken as a limitation upon the overall scope of the invention.

Example 1

Co-Polymer of 4-Methylstyrene and p-Styrenylimidohexamolybdate

This test was carried out to prepare compositions of an organic polymer bearing covalently attached organoimidopolyoxometalates as pendant groups. One such polymeric structure is shown in Scheme A.

Scheme A

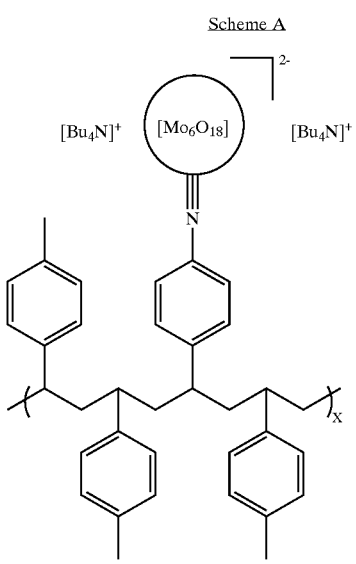

Scheme B depicts the structure of the utilized polyoxometalate monomer as determined by single-crystal x-ray diffraction, with the accompanying two tetrabutylammonium cations omitted for clarity. Bis(tetra-n-butylammonium)p-styrenylimidohexamolybdate, [(n-$C_4H_9$)$_4$N]$_2$[Mo$_6$O$_{18}$(N-p-$C_6H_4$—CH=CH$_2$)], was prepared by the Moore dissertation, *Hexamolybdate Complexes Bearing Organoimido Ligands With Remote Functionality*, Department of Chemistry, Kansas State University (1998), incorporated by reference herein.

Scheme B

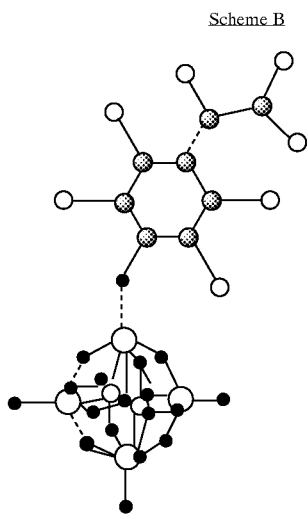

Under a nitrogen atmosphere, 0.5 g (0.34 mmol) of bis(tetra-n-butylammonium)p-styrenylimidohexamolybdate was dissolved in 5 mL of 1,2-dichloroethane in an evacuable reaction vessel to yield a dark red solution. Next, 0.16 g (1.34 mmol) of 4-methylstyrene and 10 mg (0.061 mmol) of 2,2'-azobisisobutyronitrile (AIBN, a free radical polymerization initiator) were added to the dark red solution. The reaction vessel was closed, placed in a 60° C. oil bath, and stirred for 48 hours. A dark brown, oily, insoluble residue weighing 0.435 g was separated from the dark brown dichloroethane solution by filtration. The residue was then dissolved in 10 mL of acetonitrile, filtered to remove a small amount of a gummy, insoluble material, and dried under a vacuum.

IR spectroscopy of this material confirmed the presence of the imido-substituted hexamolybdate component as revealed by its characteristic absorption pattern in the terminal Mo—O stretching region. Analysis of this material by $^1$H NMR spectroscopy in CD$_3$CN solution revealed a spectrum consistent with the expected copolymer of 4-methylstyrene and bis(tetra-n-butylammonium)p-styrenylimidohexamolybdate. That is, the characteristic vinylic $^1$H NMR resonances of both monomeric components had disappeared, broadened resonances were observed in the aryl region, and the characteristic resonances due to the tetrabutylammonium countercations of the substituted hexamolybdate were present. Integration of the relative intensities of the aryl region resonances versus that of the α-CH$_2$ resonance of the [Bu$_4$N]$^+$ cations indicated the presence of approximately three units of 4-methylstyrene per one bis(tetra-n-butylammonium)p-styrenylimidohexamolybdate unit.

Elemental analyses to determine the carbon, hydrogen, and nitrogen content of the sample gave the following results: carbon—43.10%; hydrogen—6.08%; and nitrogen—2.90%. A composition of matter incorporating an average of 2.7 units of 4-methylstyrene for each one bis(tetra-n-butylammonium)p-styrenylimidohexamolybdate unit affords an empirical formula of $C_{64.3}H_{106}N_3Mo_6O_{18}$, and requires the following: carbon—43.27%; hydrogen—5.99%; and nitrogen—2.35%. The results of the elemental analyses are thus in satisfactory agreement with the stoichiometry suggested by the $^1$H NMR spectrum.

Example 2

Co-Polymer of 4-Methylstyrene, Divinylbenzene, and p-Styrenylimidohexamolybdate

This test was carried out to demonstrate one of the manifold variabilities inherent in the invention which allows the composition and properties of the polymeric materials to be altered. In this instance, the alteration is a result of including a third component in the reaction.

Bis(tetra-n-butylammonium)p-styrenylimidohexamolybdate was prepared as described in Example 1. Under a nitrogen atmosphere, 0.5 g (0.34 mmol) of bis(tetra-n-butylammonium)p-styrenylimidohexamolybdate was dissolved in 8 mL of 1,2-dichloroethane in an evacuable reaction vessel to yield a dark red solution. Next, 0.161 g (1.36 mmol) of 4-methylstyrene, 0.048 g (0.34 mmol) of 1,4-divinylbenzene, and 20 mg (0.12 mmol) of AIBN were added to the dark red solution. The reaction vessel was closed, placed in a 60° C. oil bath, and stirred for 72 hours under a nitrogen atmosphere. The dark solution was cooled to room temperature, filtered, and dried under vacuum to yield an oily green solid which was washed with diethylether and dried under vacuum to produce a green solid. The green solid was added to 5 mL of acetonitrile to produce a green solution with an insoluble orange precipitate. The insoluble material was separated by filtration and dried under vacuum to produce an orange solid weighing 0.110 g. Evaporation of the acetonitrile solution produced a green solid weighing 0.180 g.

The orange solid was dissolved in CDCl$_3$, and its $^1$H NMR spectrum was recorded. The $^1$H NMR spectrum revealed a broadened set of resonances consistent with the expected copolymer of 4-methylstyrene, divinylbenzene, and bis(tetra-n-butylammonium)p-styrenylimidohexamolybdate, plus a signal near 2.05 ppm assignable as entrained acetonitrile. A comparison of the relative integrated intensities of the resonances due to the α-$CH_2$ resonance of the $[Bu_4N]^+$ cations versus that of the $CH_3$ resonance of the 4-methylstyrene, of the aryl region $[C_6H_4]$ protons, and of the $CH_3CN$ groups indicated an approximate ratio of one bis(tetra-n-butylammonium)p-styrenylimidohexamolybdate unit to three divinylbenzene units to sixteen 4-methylstyrene units to two $CH_3CN$ units.

Elemental analyses were carried out to determine the carbon, hydrogen, and nitrogen contents of the orange solid sample. Those contents were as follows: carbon—69.31%; hydrogen—7.01%; and nitrogen 1.92%. A composition of matter comprising one bis(tetra-n-butylammonium)p-styrenylimidohexamolybdate unit, seventeen 4-methylstyrene units, three divinylbenzene units, and 2.5 acetonitrile molecules per repeat unit gives an empirical formula of $C_{228}H_{286.5}N_{5.5}Mo_6O_{18}$ and requires the following mass composition percentages: carbon—69.02%; hydrogen—7.28%; and nitrogen—1.94%. The results of the elemental analyses are thus in satisfactory agreement with the $^1H$ NMR spectrum.

When the copolymerization of bis(tetra-n-butylammonium)p-styrenylimidohexamolybdate with 4-methylstyrene was performed in the presence of the cross-linking agent 1,4-divinylbenzene as was the case in Example 2, the $^1H$ NMR spectrum of the orange product obtained reveals considerably broadened resonances for all of the protons within the species' tetra-n-butylammonium countercations. Conversely, when the copolymerization was conducted in the absence of the 1,4-divinylbenzene cross-linking agent as was the case in Example 1, the $^1H$ NMR spectrum of the product obtained displayed sharp resonances for all of the protons within the species' tetra-n-butylammonium countercations. This observed, differentiated broadening is consistent with the formation of cross-linked networks within the product of Example 2 which provide cavities that: (1) restrict the motion of the tetra-n-butylammonium countercations; and (2) provide sites for the entrainment of the observed acetonitrile molecules. The sharp $^1H$ NMR resonances observed for the tetra-n-butylammonium countercations of the product of Example 1 are consistent with a much less restrictive, more open structure which affords the countercations the freedom to move and to rotate.

We claim:

1. A polymer comprising recurring polyoxometalate monomers represented by the formula:

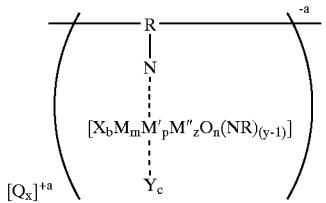

wherein:
each of M, M', and M" is a metal individually selected from the group consisting of Mo, W, V, Ti, Cr, Mn, Fe, Co, Ni, Cu, Zn, Nb, Ru, Rh, Ta, Re, and Os;
N is bonded to one of M, M', or M";
R may be the same or different in each (NR) moiety and each R is individually selected from the group consisting of substituted and unsubstituted alkyl and aryl groups other than styrene groups;
each X is individually selected from the group consisting of Si, P, B, As, Se, S, Sn, Sb, and Bi;
each Y is individually selected from the group consisting of $H_2O$ and the halides;
Y is bonded to one of M, M', or M";
each Q may be the same or different, with each Q individually being a cation;
b is a number ranging from about 0–10;
m is a number ranging from about 1–40;
each of p and z is individually a number ranging from 0–6, with the sum of m, p, and z ranging from 1–40;
n is a number ranging from about 1–200;
each a is the same number and ranges from about 1–20;
each x is a number ranging from about 1–20;
c is a number ranging from 0–2; and
y is a number ranging from about 1–20.

2. The polymer of claim 1, wherein at least one of M or M' is selected from the group consisting of Mo, W, and V, and M" selected from the group consisting of Ti, Cr, Mn, Fe, Co, Ni, Cu, Zn, Nb, Ru, Rh, Ta, Re, and Os.

3. The polymer of claim 2, wherein each of M and M' are individually selected from the group consisting of Mo, W, and V.

4. The polymer of claim 1, wherein the nitrogen atom of the (NR) moiety is bonded to one of M, M', or M" via a triple bond.

5. The polymer of claim 1, said polymer further comprising recurring olefinic monomers.

6. The polymer of claim 1, said polymer further comprising recurring monomers selected from the group consisting of substituted and unsubstituted styrene monomers, olefinic monomers, acrylates, vinylic monomers, and vinylidene monomers.

7. The polymer of claim 1, said polymer further comprising recurring monomers selected from the group consisting of methacrylates, 4-methylstyrene, divinylbenzene, and mixtures thereof.

8. The polymer of claim 1, wherein each Q is individually selected from the group consisting of $H^+$, alkali metal cations, alkaline earth metal cations, substituted and unsubstituted ammonium cations, substituted and unsubstituted phosphonium cations, and metal complex cations.

9. The polymer of claim 8, wherein at least one Q is selected from the group consisting of bis(tetra-n-butylammonium), lithium cation, and mixtures thereof.

10. A polymer comprising recurring polyoxometalate monomers represented by the formula:

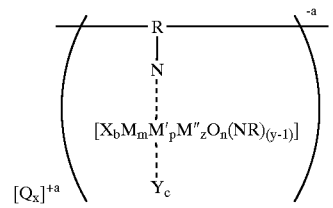

wherein:
each of M, M', and M" is a metal individually selected from the group consisting of Mo, W, V, Ti, Cr, Mn, Fe, Co, Ni, Cu, Zn, Nb, Ru, Rh, Ta, Re, and Os;

N is bonded to one of M, M', or M";

R may be the same or different in each (NR) moiety and each R is individually selected from the group consisting of substituted and unsubstituted alkyl and aryl groups other than styrene groups, substituted and unsubstituted vinyl groups, substituted and unsubstituted allyl groups, and silyl groups;

at least one R comprises a group selected from the group consisting of substituted and unsubstituted vinyl groups, substituted and unsubstituted allyl groups, and silyl groups;

each X is individually selected from the group consisting of Si, P, B, As, Se, S, Sn, Sb, and Bi;

each Y is individually selected from the group consisting of $H_2O$ and the halides;

Y is bonded to one of M, M', or M";

each Q may be the same or different, with each Q individually being a cation;

b is a number ranging from about 0–10;

m is a number ranging from about 1–40;

each of p and z is individually a number ranging from 0–6, with the sum of m, p, and z ranging from 1–40;

n is a number ranging from about 1–200;

each a is the same number and ranges from about 1–20;

each x is a number ranging from about 1–20;

c is a number ranging from 0–2; and y is a number ranging from about 1–20.

11. The polymer of claim 10, wherein said at least one R comprises a silyl group represented by the formula:

wherein:

each X' is individually selected from the group consisting of halides, alkoxides, alkyls, aryls, alkenyls, and hydrogen; and p is a number ranging from about 1–3.

12. The polymer of claim 10, wherein said at least one R comprises a vinyl group represented by the formula:

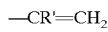

wherein R' is selected from the group consisting of hydrogen, substituted and unsubstituted alkyls, substituted and unsubstituted aryls, substituted and unsubstituted silanes, substituted and unsubstituted siloxides, substituted and unsubstituted siloxanes.

13. The polymer of claim 10, wherein said at least one R comprises an allyl group represented by the formula:

wherein each R" is individually selected from the group consisting of hydrogen, substituted and unsubstituted alkyls, substituted and unsubstituted aryls, substituted and unsubstituted silanes, substituted and unsubstituted siloxides, substituted and unsubstituted siloxanes.

14. A polymer comprising recurring polyoxometalate monomers represented by the formula:

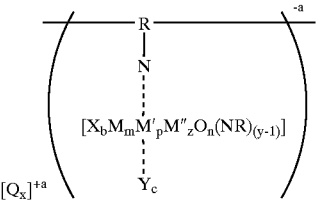

wherein:

each of M, M', and M" is a metal individually selected from the group consisting of Mo, W, V, Ti, Cr, Mn, Fe, Co, Ni, Cu, Zn, Nb, Ru, Rh, Ta, Re, and Os;

N is bonded to one of M, M', or M";

R may be the same or different in each (NR) moiety and each R is individually selected from the group consisting of substituted and unsubstituted alkyl and aryl groups;

each X is individually selected from the group consisting of Si, P, B, As, Se, S, Sn, Sb, and Bi;

each Y is individually selected from the group consisting of $H_2O$ and the halides;

Y is bonded to one of M, M', or M";

each Q may be the same or different, with each Q individually being a cation;

b is a number ranging from about 0–10;

m is a number ranging from about 1–40;

each of p and z is individually a number ranging from 0–6, with the sum of m, p, and z ranging from 1–40;

n is a number ranging from about 1–200;

each a is the same number and ranges from about 1–20;

each x is number ranging from about 1–20;

c is a number ranging from 0–2; and y is a number ranging from about 1–20; and recurring monomers selected from the group consisting of substituted and unsubstituted styrene monomers, acrylates, vinylic monomers, vinylidene monomers, and mixtures thereof.

15. A polymer comprising recurring polyoxometalate monomers represented by the formula:

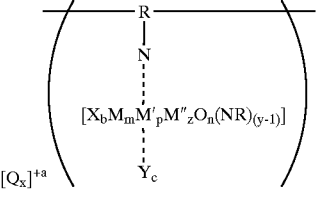

wherein:

each of M, M', and M" is a metal individually selected from the group consisting of Mo, W, V, Ti, Cr, Mn, Fe, Co, Ni, Cu, Zn, Nb, Ru, Rh, Ta, Re, and Os;

N is bonded to one of M, M', or M";

R may be the same or different in each (NR) moiety and each R is individually selected from the group consisting of substituted and unsubstituted alkyl and aryl groups;

each X is individually selected from the group consisting of Si, P, B, As, Se, S, Sn, Sb, and Bi;

each Y is individually selected from the group consisting of $H_2O$ and the halides;

Y is bonded to one of M, M', or M";

each Q may be the same or different, with each Q individually being a cation;

b is a number ranging from about 0–10;

m is a number ranging from about 1–40;

each of p and z is individually a number ranging from 0–6, with the sum of m, p, and z ranging from 1–40;

n is a number ranging from about 1–200;

each a is the same number and ranges from about 1–20;

each x is number ranging from about 1–20;

c is a number ranging from 0–2; and y is a number ranging from about 1–20; and recurring monomers selected from the group consisting of methacrylates, 4-methylstyrene, divinylbenzene, and mixtures thereof.

16. A polymer comprising recurring monomers of a polyoxometalate compound represented by the formula:

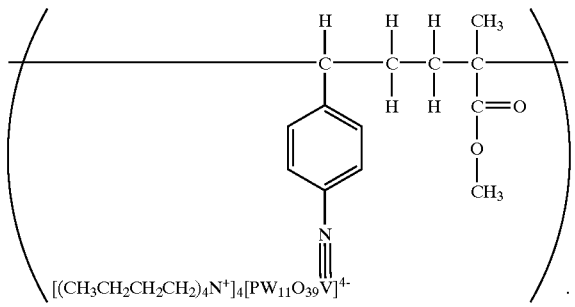

* * * * *